US007816553B2

(12) United States Patent
Storzum et al.

(10) Patent No.: US 7,816,553 B2
(45) Date of Patent: *Oct. 19, 2010

(54) CYCLOHEXANE POLYCARBOXYLIC ACID DERIVATIVES CONTAINING ADJUVANTS

(75) Inventors: Uwe Storzum, Worms (DE); Boris Breitscheidel, Limburgerhof (DE)

(73) Assignee: BASF SE (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/630,456

(22) PCT Filed: Jun. 21, 2005

(86) PCT No.: PCT/EP2005/006682

§ 371 (c)(1),
(2), (4) Date: Dec. 21, 2006

(87) PCT Pub. No.: WO2005/123821

PCT Pub. Date: Dec. 29, 2005

(65) Prior Publication Data

US 2008/0039646 A1 Feb. 14, 2008

(30) Foreign Application Priority Data

Jun. 21, 2004 (DE) .................. 10 2004 029 732

(51) Int. Cl.
C07C 69/74 (2006.01)
C08K 5/09 (2006.01)
(52) U.S. Cl. .................. 560/127; 560/129; 524/321; 524/328
(58) Field of Classification Search .................. 560/127, 560/129; 524/338, 321
See application file for complete search history.

(56) References Cited

U.S. PATENT DOCUMENTS

| 5,225,195 | A | 7/1993 | Soyama et al. | |
| 5,610,215 | A | 3/1997 | Nonweiler et al. | |
| 5,614,486 | A | 3/1997 | Giersch et al. | |
| 5,744,129 | A | 4/1998 | Dobbs et al. | |
| 5,882,636 | A | 3/1999 | Mui et al. | |
| 5,925,336 | A | 7/1999 | Garber et al. | |
| 6,284,917 | B1 * | 9/2001 | Brunner et al. ............. | 560/127 |
| 6,359,093 | B1 | 3/2002 | Takaki et al. | |
| 6,740,773 | B2 * | 5/2004 | Bohnen et al. .............. | 560/127 |
| 7,297,738 | B2 * | 11/2007 | Gosse et al. ................ | 524/285 |
| 2001/0007676 | A1 | 7/2001 | Mui et al. | |
| 2003/0146407 | A1 * | 8/2003 | Shimomura et al. .......... | 252/68 |
| 2004/0238787 | A1 * | 12/2004 | Wiese et al. ........... | 252/182.28 |
| 2004/0260113 | A1 | 12/2004 | Bueschken et al. | |
| 2005/0038285 | A1 | 2/2005 | Maschmeyer et al. | |
| 2006/0041167 | A1 | 2/2006 | Grass et al. | |
| 2006/0183936 | A1 | 8/2006 | Grass et al. | |

FOREIGN PATENT DOCUMENTS

| CA | 2376742 | 12/2000 |
| DE | 754482 | 10/1953 |
| DE | 4433854 | 3/1996 |
| DE | 19844332 | 4/2000 |
| DE | 20009445 | 9/2000 |
| DE | 10225565 | 12/2003 |
| DE | 10232868 | 2/2004 |
| EP | 0373838 | 6/1990 |
| EP | 0523122 | 1/1993 |
| EP | 0541788 | 5/1993 |
| EP | 0684037 | 11/1995 |
| EP | 0694605 | 1/1996 |
| EP | 1068862 | 1/2001 |
| GB | 843759 | 8/1960 |
| GB | 845096 | 8/1960 |
| GB | 1075254 | 7/1967 |
| JP | 52136927 | 11/1977 |
| JP | 09-249890 | 9/1997 |
| WO | WO-91/15455 | 10/1991 |
| WO | WO 91/15455 | 10/1991 |
| WO | WO-92/21720 | 12/1992 |
| WO | WO-96/03397 | 2/1996 |
| WO | WO-97/21792 | 6/1997 |
| WO | WO-98/01167 | 1/1998 |
| WO | WO-99/32427 | 7/1999 |

(Continued)

OTHER PUBLICATIONS

Reinhardt, R. et al., Defoamer Selectin i Waterborne Coatings, 1998, Journal of Coatings Technology, vol. 70, No. 885, pp. 157-160.*
Babich, et al., Health effects update, acceptable daily oral intake, and carcinogenicity of diisononylphthalate (DINP), 1998, US Consumer Products Sarety Commission, pp. 1-10.*
Oros, et al. Identification and Evaluaton of Unidentified Organic Contaminants in the San Francisco Estuary, 2002, San Francisco Estuary Institute, 86 pages.*

(Continued)

Primary Examiner—Porfirio Nazario Gonzalez
Assistant Examiner—Yate' K Cutliff
(74) Attorney, Agent, or Firm—Connolly Bove Lodge & Hutz LLP

(57) ABSTRACT

Use of cyclohexanepolycarboxylic acid derivatives in auxiliaries or as auxiliaries selected from the group consisting of the following auxiliaries:
surface-active compositions selected from flow promoters, film-forming aids, defoamers, antifoams, wetting agents, coalescers, and emulsifiers; lubricants, selected from lubricating oils, lubricating greases, and lubricating pastes; calendering auxiliaries; rheology auxiliaries, quenchers for chemical reactions; phlegmatizers; pharmaceutical products; plasticizers in adhesives; in impact modifiers, and in other modifiers, and also surface-active compositions, lubricants, calendering auxiliaries, rheology quenchers for chemical reactions, phlegmatizers, pharmaceutical products, plasticizers in adhesives; impact modifiers, and other modifiers comprising cyclohexanepolycarboxylic acid derivatives.

5 Claims, No Drawings

FOREIGN PATENT DOCUMENTS

| WO | WO-00/18516 | | 4/2000 |
|---|---|---|---|
| WO | WO-00/78853 | | 12/2000 |
| WO | WO/02/13776 | | 2/2002 |
| WO | WO-03/029168 | | 4/2003 |
| WO | WO-03/029181 | | 4/2003 |
| WO | WO 03/029339 | * | 4/2003 |
| WO | WO 03029180 | * | 4/2003 |

OTHER PUBLICATIONS

Zhang, Yuming et al., Analysis of Cis- and Trans-isomers of Perfumes by Crosslinked Glass Capillary Chromatographic Column:, Database CA Chemical Abstracts Service, Database Accession No. 107: 161353, XP002264592, SEPU 5(2), pp. 108-110, 1987 Oct. 13, 1987.

"Puchers Perfumes, Cosmetics, and Soaps" Edited by Hilda Butler, 2000, Kluwer Academic, p. 331.

U.S. Appl. No. 10/555,573, filed Jan. 4, 2007, Storzum et al.

EU Risk Assessment Report, 2 pages, 2003.

Aldrich, Catalogue Handbook of Fine Chemicals, 4 pages, 1996-1997.

Fluka, Chemika, BioChemika, 4 pages, 1997/1998.

* cited by examiner

CYCLOHEXANE POLYCARBOXYLIC ACID DERIVATIVES CONTAINING ADJUVANTS

RELATED APPLICATIONS

This application is a national stage application (under 35 U.S.C. 371) of PCT/EP2005/006682 filed Jun. 21, 2005, which claims benefit of German application 10 2004 029 732.0 filed Jun. 21, 2004.

The present invention relates to the use of 1,2-cyclohexanedicarboxylic esters as auxiliaries or in auxiliaries selected from the group consisting of surface-active compositions, calendering auxiliaries, rheology auxiliaries, quenchers for chemical reactions, phlegmatizers, pharmaceutical products, and plasticizers in adhesives, in impact modifiers, and in other modifiers.

EP-A 0 541 788 discloses the use of esters of lactic acid and 2-butoxyethanol, esters of phthalate acid and 2(2-butoxy) ethanol, methylphenylcarbinol, ethylene glycol, diethylene glycol, diacetone alcohol, propylene glycol, mono- and diethers of ethylene glycol or of propylene glycol, or a mixture thereof as flow promoters or film-forming auxiliaries in coating compositions. These flow promoters or film-forming auxiliaries improve flow and at the same time minimize foaming. However, some of these flow promoters are subject to toxicological concerns, and it is therefore desirable to replace them with compounds that are toxicologically non-hazardous. Furthermore, coating compositions can also comprise internal coalescers, e.g. butyl octyl phthalate. Because phthalates as coalescers are subject to toxicological concerns, it is likewise desirable to replace them with toxicologically non-hazardous compounds.

EP-A 0 523 122 relates to lubricant compositions which comprise synthetic esters composed of aliphatic polyols and monocarboxylic acids as additives or oil phase. It is desirable to extend the range of possible additives in order to optimize the properties of lubricant compositions with respect to their conditions of use.

Defoamers, antifoams, and wetting agents frequently comprise diesters of phthalic acid. However, these are controversial for environmental reasons, making it desirable to replace the diesters of phthalic acid with compounds non-hazardous to the environment.

The present invention therefore has the object of providing toxicologically non-hazardous compounds which can be used in a versatile manner as auxiliaries or in auxiliaries and which are suitable for the replacement of additives which may be subject to toxicological concerns, but with no adverse effect on the properties of the products in which the auxiliaries are used.

The object is achieved by the use of 1,2-cyclohexanedicarboxylic acid esters selected from the group consisting of 1,2-diisobutylcyclohexanedicarboxylic acid ester, 1,2-di-(2-ethylhexyl)-cyclohexanedi carboxylic acid ester and 1,2-diisononylcyclohexane-dicarboxylic acid ester, preferably 1,2-diisononylcyclohexanedicarboxylic acid ester, in auxiliaries or as auxiliaries selected from the group consisting of the following auxiliaries: surface-active compositions selected from flow promoters or film-forming aids, defoamers, antifoams, wetting agents, coalescers, and emulsifiers; calendering auxiliaries; rheology auxiliaries, quenchers for chemical reactions; phlegmatizers; pharmaceutical products; plasticizers in adhesives; in impact modifiers, and in other modifiers.

1,2-cyclohexanedicarboxylic acid esters have hitherto been used exclusively as plasticizers for plastics, in particular PVC (e.g. WO 00/78853), but their use in other technical sectors is hitherto almost unknown. In the following documents further uses of 1,2-cyclohexanedicarboxylic acid esters are mentioned in a general form:

DE-A 102 32 868 and DE-A 102 25 656 disclose the hydrogenation of aromatic compounds, especially the preparation of alicyclic carboxylic acids or esters thereof by hydrogenation of the core of the corresponding aromatic polycarboxylic acids or esters thereof as well as suitable hydrogenation catalysts. The polycarboxylic esters prepared by the hydrogenation processes disclosed in DE-A 102 32 868 and DE-A 102 25 656 are useful besides their use as plasticizers as component in lubricating oil, as component in cutting oil and as component in fluids for metal working. Further, the polycarboxylic esters are useful as components of paints, varnish, inks and adhesives.

WO 03/029168 discloses mixtures of alicyclic polycarboxylic esters having a high cis isomer content, which are prepared by means of core hydrogenation of the corresponding aromatic polycarboxylic acid esters. Besides the use as plasticizers the use of the alicyclic polycarboxylic esters as component in lubricating oil, as component in cutting oil and as component in fluids for metal working is disclosed in WO 03/029168 in general terms.

WO 03/029181 discloses mixtures of alicyclic polycarboxylic esters having a trans isomer proportion greater than 10 mol-%, which are prepared by means of core hydrogenation of the corresponding aromatic polycarboxylic acid esters. Besides the use as plasticizers the use of the alicyclic polycarboxylic esters as component in lubricating oil, as component in cutting oil and as component in fluids for metal working is disclosed in WO 03/029181 in general terms.

JP-A 09 249 890 discloses specific aliphatic cyclic carboxylic acid esters as lubricating oil for metal working. The aliphatic carboxylic acid esters may be cyclohexane carboxylic acid esters or cyclohexene carboxylic acid esters.

According to the present application it has been found that specific 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester are suitable as or in auxiliaries for various other applications not mentioned in the state of the art.

For the purposes of the present invention, other suitable compounds are the esters of cyclohexane-1,2-dicarboxylic acid disclosed in WO 99/32427 and again listed below:

di(isononyl) esters of cyclohexane-1,2-dicarboxylic acid obtainable via hydrogenation of a di(isononyl) phthalate with the CAS No. 68515-48-0;

di(isononyl) esters of cyclohexane-1,2-dicarboxylic acid obtainable via hydrogenation of a di(isononyl) phthalate with the CAS No. 28553-12-0, based on n-butene;

di(isononyl) esters of cyclohexane-1,2-dicarboxylic acid obtainable via hydrogenation of a di(isononyl) phthalate with the CAS No. 28553-12-0, based on isobutene;

a 1,2-di-$C_9$ ester of cyclohexanedicarboxylic acid obtainable via hydrogenation of a di(nonyl) phthalate with the CAS No. 68515-46-8.

The content of WO 99/32427 which published as U.S. Pat. No. 6,284,917 relating inter alia to these compounds listed immediately above and to the preparation of cyclohexanepolycarboxylic acids using specific macroporous catalysts is incorporated in its entirety into the present application by way of reference.

Other suitable compounds for the purposes of the present invention are the hydrogenation products of the commercially available benzenecarboxylic esters with the trade names JAY- FLEX™ DINP (CAS No. 68515-48-0), JAYFLEX™ DIDP (CAS No. 68515-49-1), PALATINOL® 9-P, VESTINOL® 9 (CAS No. 28553-12-0), JAYFLEX™ DIOP (CAS No. 27554-26-3), Witamol 110 (CAS No. 90193-91-2) and UNI-MOLL® BB (CAS No. 85-68-7). JAYFLEX™ are plasticizers that are phthalate esters made by ExxonMobile Chemical Company. BASF's PALATINOL® are plasticizers which include C7 to C11 linear phthalates. Degussa's VESTINOL® is a di-iso-nonyl phthalate (DINP). WITAMOL is a (di-n-C6-C10-alkyl phthalate) Lanxess Deutschland GmbH's UNI-MOLL® is a butyl benzyl phthalate (BBP).

Depending on the specific application sector, particular preference is given to dialkyl esters of 1,2-cyclohexanedicarboxylic acid with different alkyl groups R. In flow promoters and film-forming auxiliaries, or as flow promoters and film-forming auxiliaries, and in phlegamatizers or as phlegamatizers, and in adhesives or as adhesives, it is particularly preferable to use 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester, wherein the 1,2-cyclohexanedicarboxylic acid esters preferably comprise diisobutyl radicals. In coalescers or as coalescers, in defoamers and antifoams, or as defoamers and antifoams, in wetting agents or as wetting agents, in lubricants or as lubricants, and in detergents it is particularly preferable to use 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester, wherein the 1,2-cyclohexanedicarboxylic acid esters preferably comprise 2-ethylhexyl radicals oder diisononyl radicals. In emulsifiers or as emulsifiers, and in impact modifiers or as impact modifiers, it is particularly preferable to use 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-di-isononylcyclohexanedicarboxylic acid ester, wherein the 1,2-cyclohexanedicarboxylic acid esters preferably comprise 2-ethylhexyl radicals oder diisononyl radicals. In calendering auxiliaries and rheology auxiliaries, or as calendering auxiliaries or rheology auxiliaries, in quenchers or as quenchers, in pharmaceutical compositions, or in time-release compositions it is particularly preferable to use 1,2-cyclohexanedicarboxylic acid esters selected from the group consisting of 1,2-diisobutylcyclohexanedicarboxylic acid ester, 1,2-di-(2-ethythexyl)-cyclohexanedicarboxylic acid ester and 1,2-di-isononylcyclohexanedicarboxylic acid ester, wherein the 1,2-cyclohexanedicarboxylic acid esters preferably comprise diisobutyl radicals.

The 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester are preferably prepared according to the process disclosed in WO 99/32427. This process comprises the hydrogenation of a benzenepolycarboxylic acid or of a derivative thereof, or the hydrogenation of a mixture composed of two or more thereof, by bringing the benzenepolycarboxylic acid or the derivative thereof or the mixture composed of two or more thereof into contact with a hydrogen-containing gas in the presence of a catalyst which comprises, as active metal, at least one metal of the 8th transition group of the Periodic Table of the Elements alone or together with at least one metal of 1st or 7th transition group of the Periodic Table of the Elements, applied to a support which has macropores.

In one preferred embodiment, the support has an average pore diameter of at least 50 nm and a BET surface area of not more than 30 m$^2$/g, and the amount of the active metal is from 0.01 to 30% by weight, based on the total weight of the catalyst.

In another embodiment, use is made of a catalyst where the amount of the active metal is from 0.01 to 30% by weight, based on the total weight of the catalyst, and where from 10 to 50% of the pore volume of the support comprises macropores with a pore diameter in the range from 50 nm to 10 000 nm, and from 50 to 90% of the pore volume of the support comprises mesopores with a pore diameter in the range from 2 to 50 nm, the total of the proportions of the pore volumes being 100%.

In another embodiment, the catalyst comprises from 0.01 to 30% by weight, based on the total weight of the catalyst, of an active metal, applied to a support, where the support has an average pore diameter of at least 0.1 μm and a BET surface area of at most 15 m$^2$/g. In principle, use may be made of any of the supports which have macropores, i.e. supports which have exclusively macropores, or else those which comprise not only macropores but also meso- and/or micropores.

The active metal used may in principle be any of the metals of the 8th transition group of the Periodic Table of the Elements. It is preferable for the active metals used to be platinum, rhodium, palladium, cobalt, nickel or ruthenium, or a mixture composed of two or more thereof, and ruthenium is in particular used as active metal. Among the metals of the 1st or 7th, or the 1st and the 7th, transition group of the Periodic Table which can also be used, preference is given to the use of copper and/or rhenium, but in principle any of these metals may be used.

For the purposes of the present invention, the definitions of the terms "macropores" and "mesopores" are those given in Pure Appl. Chem., 45 p. 79 (1976), i.e. pores whose diameter is above 50 nm (macropores) or from 2 to 50 nm, (mesopores).

The content of the active metal is generally from 0.01 to 30% by weight, preferably from 0.01 to 5% by weight, particularly preferably from 0.1 to 5% by weight, based in each case on the total weight of the catalyst used.

The term "benzenepolycarboxylic acid or a derivative thereof" used in WO 99/32427 comprises any of the benzenepolycarboxylic acids themselves, e.g. phthalic acid, isophthalic acid, terephthalic acid, trimellitic acid, trimesic acid, hemimellitic acid, and pyromellitic acid, and derivatives thereof, and mention may be made in particular here of mono-, di-, tri- and tetraesters, in particular alkyl esters, and anhydrides. Preference is given to the alkyl esters of the acids mentioned, the alkyl group preferably being a radical R defined above.

The method of preparing those 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexane-dicarboxylic acid ester whose use is preferred is generally reaction of benzenepolycarboxylic acids with the alcohols corresponding to the alkyl groups of the esters. The person skilled in the art is aware of suitable reaction conditions for the reaction of the benzenepolycarboxylic acids with the corresponding alcohols.

The present invention therefore also provides the use of 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester as auxiliaries or in auxiliaries selected from the group consisting of surface-active compositions, calendering auxiliaries, rheology auxiliaries, quenchers for chemical reactions, phlegmatizers, pharmaceutical products, plasticizers in adhesives, in impact modifiers, and in other modifiers, where the 1,2-cyclohexanedicarboxylic acid esters can be prepared by the following process a) esterification of phthalic acid with one or more alcohols of the formula

R—OH where

R isobutyl, 2-ethylhexyl or isononyl, giving a phthalic acid ester of the formula III

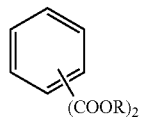
(COOR)$_2$
(III)

b) hydrogenation of the phthalic acid ester of the formula III to give a corresponding 1,2-cyclohexanedicarboxylic acid ester.

One preferred embodiment of the hydrogenation of the phthalic acid ester of the formula III (step b)) has been mentioned above.

Phthalic acid is used as benzenepolycarboxylic acid Phthalic acid is available commercially.

The alcohols used are preferably the alcohols corresponding to the radical R=isobutyl, 2-ethylhexyl or isononyl of the 1,2-cyclohexanedicarboxylic acid esters used according to the present invention. Therefore isobutanol (isobutyl alcohol), 2-ethylhexanol (2-ethylhexyl alcohol) or isononanol (isononyl alcohol; C9-alcohol) are used. The alcohol used for the esterification with the phthalic acid may be—in the case of isononanol—the individual C9-alcohol isomer corresponding to the abovementioned isononyl radical R, or may be a mixture of different C9-alcohols having isomeric alkyl radicals having the same number of carbon atoms. Isobutanol and 2-ethylhexanol are each single isomers, e.g. alcohols with an isobutyl resp. 2-ethylhexyl radical.

The alcohols or alcohol mixtures suitable for the reaction with the benzenepolycarboxylic acids may be prepared by any of the processes known to the person skilled in the art. Examples of suitable processes for the preparation of alcohols, or steps of processes used in the preparation of alcohols are:

hydroformylation with subsequent hydrogenation of the aldehydes formed, for example as disclosed in WO 92/13818, DE-A 2 009 505, DE-A 199 24 339, EP-A 1 113 034, WO 00/63151, WO 99/25668, JP-A 1 160 928, JP-A 03 083 935, JP-A 2000/053803, EP-A 0 278 407, EP-A 1 178 029, FR-A 1 304 144, JP-A 30 44 340, JP-A 30 44 341, JP-A 30 44 342, JP-A 0 40 36 251, GB-A 721,540, DE-A 195 304 14, JP-A 2001/049029, U.S. Pat. No. 2,781,396, U.S. Pat. No. 3,094,564, FR-A 1 324 873, JP-A 0 816 9854, U.S. Pat. No. 3,153,673, U.S. Pat. No. 3,127,451, U.S. Pat. No. 1,828,344, WO 2003/66642, WO 2003/18912, EP-A 0 424 767, WO 2002/68369, EP-A 0 366 089, JP-A 2001/002829, DE-A 100 35 617, DE-A 199 55 593, WO 2002/00580, EP-A 0 643 031, U.S. Pat. No. 2,876,264, JP-A 2000/319444, and DE-A 100 32 580;

hydrogenation of aldol products, for example as disclosed in DE-A 102 51 311, JP-A 05 194 761, U.S. Pat. No. 3,272,873, DE-A 3 151 086, JP-A 2001/322959, WO 98/03462, and EP-A 0 603 630;

hydration of alkenes, e.g. as disclosed in U.S. Pat. No. 5,136,108, EP-A 0 325 144, EP-A 0 325 143, DE-A 100 50 627, U.S. Pat. No. 4,982,022, GB-A 2,187,741, DE-A 36 28 008, U.S. Pat. No. 3,277,191, JP-A 2000/191 566, DE-A 854 377, DE-A 38 01 275, DE-A 39 25 217, JP-A 06 321 828, JP-A 02 088 536, JP-A 06 287 156, JP-A 06 287 155, JP-A 54 141 712, JP-A 08 283 186, JP-A 09 263 558, and U.S. Pat. No. 4,684,751;

hydrogenation of carboxylic acids and carboxylic esters, in particular fatty acids and fatty acid esters, for example as disclosed in U.S. Pat. No. 5,463,143, U.S. Pat. No. 5,475,159, WO 94/10112, CA 2,314,690, WO 94/06738, JP-A 06 065 125, and U.S. Pat. No. 3,361,832;

hydrogenation of unsaturated alcohols or of carbonyl compounds, for example as disclosed in EP-A 0 394 842, DE-A 1 269 605, WO 88/05767, FR-A 1,595,013, EP-A 0 326 674, BE-A 756 877, BE-A 757 561, DE-A 1 277 232, FR-A 1,499,041, and DE-A 1 276 620;

hydrogenation of epoxides, for example as disclosed in FR-A 1,508,939, GB-A 879 803, and DE-A 1 078 106;

processes comprising a telomerization step, for example as disclosed in EP-A 0 330 999, DE-A 1 138 751, U.S. Pat. No. 5,908,807, NE-6,603,884, and U.S. Pat. No. 3,091,628, processes comprising an isomerization step, for example as disclosed in DE-A 42 28 887;

hydrolysis of sulfates, for examples as disclosed in GB-A 1,165,309;

reaction of dienes with amines, for example as disclosed in DE-A 44 31 528;

enzymatic preparation of alcohols, for example as disclosed in WO 93/24644;

selective hydrogenation of dienes, for example as disclosed in U.S. Pat. No. 3,203,998, DE-A 21 41 186, GB-A 2,093,025, JP-A 02 129 24, JP-A 1 122 8468, DE-A 195 44 133, WO 94/00410, GB-A 2,260,136, DE-A 44 10 746, and JP-A 08 176 036;

preparation of alcohols from nitriles, for example as disclosed in EP-A 0 271 092;

preparation of alcohols via reaction of alkynes, for example as disclosed in RU 205 9597-C1; and hydrogenolysis of substituted tetrahydropyrans, for example as disclosed in GB 1,320,188.

The person skilled in the art is aware of other processes for preparing alcohols which can likewise be used for the preparation of alcohol mixtures or alcohols suitable for the esterification with phthalic acid. As mentioned above, alcohols are isobutanol, 2-ethylhexanol and isononanol. In particular, 2-ethylhexanol and isononanol are particularly preferably prepared via catalytic hydroformylation (also termed oxo reaction) of olefins and subsequent hydrogenation of the aldehydes formed. A person skilled in the art is aware of suitable hydroformylation processes, which are disclosed in the above-mentioned documents. The alcohol mixtures and alcohols disclosed in the documents mentioned may be reacted with the abovementioned phthalic acid to give the desired 1,2-cyclohexanedicarboxylic acid esters and, respectively, mixtures of these esters.

Mixtures comprising $C_8$ alcohols and processes for their preparation are disclosed by way of example in GB-A 721 540, which describes a process for the preparation of isooctyl alcohols starting from heptenes by means of hydroformylation and subsequent hydrogenation. Other documents which disclose the preparation of $C_7$ alcohols or of mixtures comprising these alcohols are DE-A 195 30 414, JP-A 2001/49029, U.S. Pat. No. 2,781,396, U.S. Pat. No. 3,094,564, FR-A 1,324,873, JP-A 08 169 854, U.S. Pat. No. 3,153,673, U.S. Pat. No. 3,127,451, and U.S. Pat. No. 1,828,344.

C9 alcohols or mixtures comprising $C_9$ alcohols are preferably prepared via dimerization of butenes, hydroformylation of the resultant octenes, and subsequent hydrogenation of the resultant $C_9$ aldehyde.

Suitable processes and mixtures comprising $C_9$ alcohols are disclosed by way of example in WO 92/13818, DE-A 20 09 505, DE-A 199 24 339, EP-A 1 113 034, WO 2000/63151, WO 99/25668, JP-A 1 160 928, JP-A 03 083 935, JP-A 2000/053803, EP-A 0 278 407, and EP-A 1 178 029.

It is possible that although the alkyl groups of the alkyl esters of the cyclohexanediisononyl ester have the same number of carbon atoms, they have different types of branching, thus forming isomer mixtures. The proportion of the different isomers of the alkyl groups is generally the result of the composition of the C9-alcohol used for the esterification of the phthalic acid which, after esterification, are hydrogenated to give the corresponding cyclohexanedicarboxylic acid esters. Suitable alcohol mixtures have been mentioned above. For the purposes of the present application, therefore, branched alkyl radicals having a certain number of carbon atoms are not only each of the individual isomers used but also isomer mixtures whose composition results—as mentioned above—from the composition of the alcohols used for the esterification of the phthalic acid. The isobutyl radical and the 2-ethylhexyl radical which are radicals of the 1,2-diisobutylcyclohexanedicarboxylic acid ester and the 1,2-di-(2-ethylhexyl)-cyclohexanedicarboxylic acid ester used according to the present invention each are—as mentioned before—defined radicals and not—as is possible for the isononyl radical—isomeric mixtures.

The person skilled in the art is aware of the preparation of the abovementioned isobutanol and 2-ethylhexanol.

If the alkyl radicals R of the 1,2-cyclohexanedicarboxylic acid esters is an isononyl radical radical, it is preferable to use isononanols (C9-alcohols) which have degrees of branching (ISO index) which are generally from 0.10 to 4, preferably from 0.5 to 3, particularly preferably from 0.8 to 2, and in particular from 1 to 1.5, meaning that each of the alcohols is generally a mixture of different isomers. It is very particularly preferable to use $C_9$ alcohol mixtures with an ISO index of from 1 to 1.5, in particular nonanol mixtures with an ISO index of 1.25 or 1.6.

The ISO index is a dimensionless variable determined by means of gas chromatography.
Method: Capillary GC
Apparatus: Capillary gas chromatograph with autosampler, split/splitless injection system, and flame ionization detector (FID)
Chemicals:—MSTFA (N-methyl-N-trimethylsilyltrifluoroacetamide)
Comparisons for determining retention times
Specimen preparation: 3 drops of the specimen are kept at 80° C. for 60 minutes in 1 ml of MSTFA
GC conditions: Capillary column: Ultra-1
Length: 50 m
Internal diameter: 0.25 mm
Film thickness: 0.1 micrometer
Carrier gas: helium
Column inlet pressure: 200 psi, constant
Split: 80 ml/min
Septum flushing: 3 ml/min
Oven temperature: 120° C., 25 min, isothermic
Injector temperature: 250° C.
Detector temperature: 250° C. (FID)
Injection volume: 0.5 microliter
Calculation The following table shows the procedure for calculating the ISO index:

| Component | Name | Branching | Proportion in % index | Index |
|---|---|---|---|---|
| 1 | 2-ethyl-2-methyl-1-hexanol | 2 | 1.00 | 0.0200 |
| 2 | 2-ethyl-4-methyl-1-hexanol | 2 | 1.00 | 0.0200 |
| 3 | 2-ethyl-4-methyl-1-hexanol | 2 | 1.00 | 0.0200 |
| 4 | 2-propyl-3-methyl-1-pentanol | 2 | 1.00 | 0.0200 |
| 5 | 2-propyl-1-hexanol | 1 | 1.00 | 0.0100 |
| 6 | 2,5-dimethyl-1-heptanol | 2 | 1.00 | 0.0200 |
| 7 | 2,3-dimethyl-1-heptanol | 2 | 1.00 | 0.0200 |
| 8 | 2,3,4-trimethyl-1-hexanol | 3 | 1.00 | 0.0300 |
| 9 | 2-ethyl-1-heptanol | 1 | 1.00 | 0.0100 |
| 10 | 3-ethyl-4-methyl-1-hexanol | 2 | 82.00 | 1.6400 |
| 11 | 3-ethyl-1-heptanol | 1 | 1.00 | 0.0100 |
| 12 | 2-methyl-1-octanol | 1 | 1.00 | 0.0100 |
| 13 | 4,5-dimethyl-1-heptanol | 2 | 1.00 | 0.0200 |
| 14 | 4,5-dimethyl-1-heptanol | 2 | 1.00 | 0.0200 |
| 15 | 4-methyl-1-octanol | 1 | 1.00 | 0.0100 |
| 15a | 7-methyl-1-octanol | 1 | 1.00 | 0.0000 |
| 16 | 6-methyl-1-octanol | 1 | 1.00 | 0.0100 |
| 17 | 1-nonanol | 0 | 1.00 | 0.0000 |
| | | Total: | 99.00 | 1.9000 |
| | Unknown component | 2 | 1.00 | 0.0200 |
| | | | ISO index: | 1.9200 |

The ISO index is therefore calculated from the degree of branching of the components in the alcohol mixture and the amount of the corresponding component (determined by gas chromatography).

The isononanols are prepared in accordance with the abovementioned processes. For the preparation of cyclohexanepolycarboxylic esters where R is 9, it is particularly preferable to use a nonanol mixture where from 0 to 20% by weight, preferably from 0.5 to 18% by weight, particularly preferably from 6 to 16% by weight, of the nonanol mixture has no branching point, and from 5 to 90% by weight, preferably from 10 to 80% by weight, particularly preferably from 45 to 75% by weight, has one branching point, and from 5 to 70% by weight, preferably from 10 to 60% by weight, particularly preferably from 15 to 35% by weight, has two branching points, and from 0 to 10% by weight, preferably from 0 to 8% by weight, particularly preferably from 0 to 4% by weight, has three branching points, and from 0 to 40% by weight, preferably from 0.1 to 30% by weight, particularly preferably from 0.5 to 6.5% by weight is other components. These other components are generally nonanols having more than three branching points, decanols, or octanols, and the entirety of the components mentioned here is 100% by weight.

One particularly preferred embodiment of a nonanol mixture used for the preparation of cyclohexanepolycarboxylic acid derivatives whose use is preferred has the following composition:

from 1.73 to 3.73% by weight, preferably from 1.93 to 3.53% by weight, particularly preferably from 2.23 to 3.23% by weight, of 3-ethyl-6-methylhexanol;

from 0.38 to 1.38% by weight, preferably from 0.48 to 1.28% by weight, particularly preferably from 0.58 to 1.18% by weight, of 2,6-dimethylheptanol;

from 2.78 to 4.78% by weight, preferably from 2.98 to 4.58% by weight, particularly preferably from 3.28 to 4.28% by weight, of 3,5-dimethylheptanol;

from 6.30 to 16.30% by weight, preferably from 7.30 to 15.30% by weight, particularly preferably from 8.30 to 14.30% by weight, of 3,6-dimethylheptanol;

from 5.74 to 11.74% by weight, preferably from 6.24 to 11.24% by weight, particularly preferably from 6.74 to 10.74% by weight, of 4,6-dimethylheptanol;

from 1.64 to 3.64% by weight, preferably from 1.84 to 3.44% by weight, particularly preferably from 2.14 to 3.14% by weight, of 3,4,5-trimethylhexanol;

from 1.47 to 5.47% by weight, preferably from 1.97 to 4.97% by weight, particularly preferably from 2.47 to 4.47% by weight, of 3,4,5-trimethylhexanol, 3-methyl-4-ethylhexanol, and 3-ethyl-4-methylhexanol;

from 4.00 to 10.00% by weight, preferably from 4.50 to 9.50% by weight, particularly preferably from 5.00 to 9.00% by weight, of 3,4-dimethylheptanol;

from 0.99 to 2.99% by weight, preferably from 1.19 to 2.79% by weight, particularly preferably from 1.49-2.49% by weight, of 4-ethyl-5-methylhexanol, and 3-ethylheptanol;

from 2.45 to 8.45% by weight, preferably from 2.95 to 7.95% by weight, particularly preferably from 3.45 to 7.45% by weight, of 4,5-dimethylheptanol, and 3-methyloctanol;

from 1.21 to 5.21% by weight, preferably from 1.71 to 4.71% by weight, particularly preferably from 2.21 to 4.21% by weight, of 4,5-dimethylheptanol;

from 1.55 to 5.55% by weight, preferably from 2.05 to 5.05% by weight, particularly preferably from 2.55 to 4.55% by weight, of 5,6-dimethylheptanol;

from 1.63 to 3.63% by weight, preferably from 1.83 to 3.43% by weight, particularly preferably from 2.13 to 3.13% by weight, of 4-methyloctanol;

from 0.98 to 2.98% by weight, preferably from 1.18 to 2.78% by weight, particularly preferably from 1.48 to 2.48% by weight, of 5-methyloctanol;

from 0.70 to 2.70% by weight, preferably from 0.90 to 2.50% by weight, particularly preferably from 1.20 to 2.20% by weight, of 3,6,6-trimethylhexanol;

from 1.96 to 3.96% by weight, preferably from 2.16 to 3.76% by weight, particularly preferably from 2.46 to 3.46% by weight, of 7-methyloctanol;

from 1.24 to 3.24% by weight, preferably from 1.44 to 3.04% by weight, particularly preferably from 1.74 to 2.74% by weight, of 6-methyloctanol;

from 0.1 to 3% by weight, preferably from 0.2 to 2% by weight, particularly preferably from 0.3 to 1% by weight, of n-nonanol;

from 25 to 35% by weight, preferably from 28 to 33% by weight, particularly preferably from 29 to 32% by weight, of other alcohols having 9 or 10 carbon atoms, the entirety of the components mentioned giving 100% by weight.

Another particularly preferred embodiment of a nonanol mixture used for the preparation of cyclohexanepolycarboxylic acid derivatives whose use is preferred has the following composition:

from 6.0 to 16.0% by weight, preferably from 7.0 to 15.0% by weight, particularly preferably from 8.0 to 14.0% by weight, of n-nonanol;

12.8 to 28.8% by weight, preferably from 14.8 to 26.8% by weight, particularly preferably from 15.8 to 25.8% by weight, of 6-methyloctanol;

12.5 to 28.8% by weight, preferably from 14.5 to 26.5% by weight, particularly preferably from 15.5 to 25.5% by weight, of 4-methyloctanol;

3.3 to 7.3% by weight, preferably from 3.8 to 6.8% by weight, particularly preferably from 4.3 to 6.3% by weight, of 2-methyloctanol;

5.7 to 11.7% by weight, preferably from 6.3 to 11.3% by weight, particularly preferably from 6.7 to 10.7% by weight, of 3-ethylheptanol;

1.9 to 3.9% by weight, preferably from 2.1 to 3.7% by weight, particularly preferably from 2.4 to 3.4% by weight, of 2-ethylheptanol;

1.7 to 3.7% by weight, preferably from 1.9 to 3.5% by weight, particularly preferably from 2.2 to 3.2% by weight, of 2-propylhexanol;

3.2 to 9.2% by weight, preferably from 3.7 to 8.7% by weight, particularly preferably from 4.2 to 8.2% by weight, of 3,5-dimethylheptanol;

6.0 to 16.0% by weight, preferably from 7.0 to 15.0% by weight, particularly preferably from 8.0 to 14.0% by weight, of 2,5-dimethylheptanol;

1.8 to 3.8% by weight, preferably from 2.0 to 3.6% by weight, particularly preferably from 2.3 to 3.3% by weight, of 2,3-dimethylheptanol;

0.6 to 2.6% by weight, preferably from 0.8 to 2.4% by weight, particularly preferably from 1.1 to 2.1% by weight, of 3-ethyl-4-methylhexanol;

2.0 to 4.0% by weight, preferably from 2.2 to 3.8% by weight, particularly preferably from 2.5 to 3.5% by weight, of 2-ethyl-4-methylhexanol;

0.5 to 6.5% by weight, preferably from 1.5 to 6% by weight, particularly preferably from 1.5 to 5.5% by weight, of other alcohols having 9 carbon atoms;

where the entirety of the components mentioned gives 100% by weight.

The present application also provides 1,2-cyclohexanedicarboxylic acid esters capable of preparation via a process comprising the steps of a) esterification of phthalic acid
with one or more alcohols of the formula

where
R' is isobutyl, 2-ethylhexyl or isononyl,
where—in the case of isononyl—the alkyl radicals R' have degrees of branching of from 0.1 to 4, preferably from 0.5 to 3, particularly preferably from 0.8 to 2, very preferably from 1 to 1.5 (ISO index),
giving phthalic acid ester of the formula III'

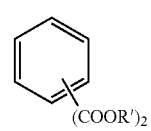

(III')

b) hydrogenation of the phthalic acid ester of the formula III' to give a corresponding cyclohexanecarboxylic ester.

Preferred alcohols R'—OH, in particular nonanol mixtures, are the abovementioned alcohols and alcohol mixtures.

The inventive 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester have particularly good suitability as or in auxiliaries according to the present application.

The 1,2-cyclohexanedicarboxylic acid esters used according to the invention are in particular suitable for use in surface-active compositions selected from the group consisting of flow promoters, film-forming auxiliaries, defoamers, antifoams, wetting agents, coalescers, and emulsifiers.

The present application therefore also provides surface-active compositions selected from the group consisting of flow promoters, film-forming auxiliaries, defoamers, antifoams, wetting agents, coalescers, and emulsifiers, comprising at least one 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester.

The person skilled in the art is aware of the composition of each of the surface-active compositions, and also of preferred amounts of the individual components of the compositions. The 1,2-cyclohexanedicarboxylic acid esters used according to the invention may also be used alone, without other additional compounds, to form surface-active compositions.

Flow promoters or film-forming auxiliaries are suitable for improving flow and for minimizing foaming. They are preferably used in coating compositions, in amounts usual for conventional flow promoters and for conventional film-forming auxiliaries. The person skilled in the art is aware of suitable compositions and suitable amounts of flow promoters and of film-forming auxiliaries in coating compositions.

An 1,2-cyclohexanedicarboxylic acid ester preferably used in the flow promoters and film-forming auxiliaries, or as flow promoters and film-forming auxiliaries is 1,2-diisobutylcyclohexanedicarboxylic acid ester.

The 1,2-cyclohexanedicarboxylic acid esters selected from the group consisting of 1,2-diisobutylcyclohexanedicarboxylic acid ester, 1,2-di-(2-ethylhexyl)-cyclohexane-dicarboxylic acid ester and 1,2-diisononylcyclohexanedicarboxylic acid ester used according to the invention are moreover suitable as internal coalescers which may likewise be used in coating compositions and suitable amounts of flow promoters and film-forming auxiliaries used therein. The amounts of the 1,2-cyclohexanedicarboxylic acid esters used in the coating compositions are those conventional and known to the person skilled in the art for conventional coalescers.

1,2-di-(2-ethylhexyl)-cyclohexanedicarboxylic acid ester and 1,2-diisononylcyclohexanedicarboxylic acid ester are preferably used in the coalescers, or as coalescers.

The 1,2-cyclohexanedicarboxylic acid esters selected from the group consisting of 1,2-diisobutylcyclohexanedlcarboxylic acid ester, 1,2-di-(2-ethylhexyl)cyclohexanedicarboxylic acid ester and 1,2-diisononylcyclohexanedicarboxylic acid ester used according to the invention may moreover be used as defoamers or antifoams. These defoamers or antifoams are likewise used, by way of example, in coating compositions. The defoamers and antifoams may moreover be used as additives in detergent compositions and in cleaning compositions, and also in other defoaming liquids. The 1,2-cyclohexanedicarboxylic acid esters are used in the amounts conventional for conventional defoamers or antifoams. Suitable amounts of defoamers or antifoams, depending on the intended use, are readily determined by the person skilled in the art. Further information concerning defoamers is disclosed, by way of example, in Ullmann (4th) 20, 411-414, and information concerning antifoams is disclosed by way of example in Adhäsion 29, 21 (1985).

1,2-di-(2-ethylhexyl)-cyclohexanedicarboxylic acid ester and 1,2-diisononylcyclohexanedicarboxylic acid ester are preferably used in the defoamers or antifoams, or as defoamers and antifoams.

The 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester used according to the invention may moreover be used in or as wetting agents. These wetting agents serve in particular as auxiliaries (additives) in the textile industry. When 1,2-cyclohexanedicarboxylic acid esters are used in or as wetting agents, their amounts used are amounts conventional for conventional wetting agents, and are known- to the person skilled in the art.

1,2-di-(2-ethylhexyl)-cyclohexanedicarboxylic acid ester and 1,2-diisononylcyclohexanedicarboxylic acid ester are preferably used in the wetting agents, or as wetting agents.

The present application also provides the use of the 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester used according to the invention as emulsifiers. The 1,2-cyclohexanedicarboxylic acid esters may be used here to form emulsions for any desired intended purpose. When 1,2-cyclohexanedicarboxylic acid esters are used as emulsifier, their used amounts are those conventional for conventional emulsifiers. These depend on the intended use and are known to the person skilled in the art.

1,2-di-(2-ethylhexyl)-cyclohexanedicarboxylic acid ester and 1,2-diisononylcyclohexanedicarboxylic acid ester are preferably used in the emulsifiers, or as emulsifiers.

The amount used of the 1,2-cyclohexanedicarboxylic acid esters when they are used in or as surface-active compositions is generally up to 50% by weight, based on the respective composition in which the 1,2-cyclohexanedicarboxylic acid esters are used in or as surface-active compositions. The proportion of the at least one 1,2-cyclohexanedicarboxylic acid esters derivative is preferably from 0.01 to 10% by weight, particularly preferably from 0.1 to 5% by weight.

The 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid esters according to the present application may also be used as calendering auxiliaries or rheology auxiliaries. If the 1,2-cyclohexanedicarboxylic acid esters are used as calendering auxiliaries, these can improve the slip properties and adhesion properties during processing of the plastic to be processed. If the 1,2-cyclohexanedicarboxylic acid esters are used as calendering auxiliaries or rheology auxiliaries, the amounts are the amounts conventionally used in relation to conventional calendering or rheology auxiliaries and are known to the person skilled in the art.

1,2-diisobutylcyclohexanedicarboxylic acid ester is preferably used in the calendering auxiliaries or rheology auxiliaries, or as calendering auxiliaries or rheology auxiliaries.

The present application also provides the use of the 1,2-cyclohexanedicarboxylic acid esters selected from the group consisting of 1,2-diisobutylcyclohexanedicarboxylic acid ester, 1,2-di-(2-ethythexyl)-cyclohexanedicarboxylic acid ester and 1,2-diisononylcyclohexanedicarboxylic acid ester according to the present invention as quenchers for chemical reactions or phlegmatizers.

The present invention therefore also provides quenchers for chemical reactions or phlegmatizers comprising at least one 1,2-cyclohexanedicarboxylic acid ester, preferably at least 1,2-cyclohexanedicarboxylic acid ester disclosed according to the present application. The quencher or the phlegmatizer here may comprise the at least one cyclohexanepolycarboxylic acid derivative as sole component or one of two or more components.

If the 1,2-cyclohexanedicarboxylic acid esters is used as quencher for chemical reactions, preferred chemical reactions are the synthesis of acrylic acid or of maleic anhydride. Reactive intermediates or products can be scavenged from the gas phase with the aid of the 1,2-cyclohexanedicarboxylic acid ester used according to the invention. Because the 1,2-cyclohexanedicarboxylic acid esters used according to the invention have excellent solvating power for reactive intermediates and, respectively, for the products, they can be used advantageously. The amount of 1,2-cyclohexanedicarboxylic acid ester is the amount conventionally used for conventional quenchers and is known to the person skilled in the art.

1,2-diisobutylcyclohexanedicarboxylic acid ester is preferably used in the calendering auxiliaries or rheology auxiliaries, or as calendaring auxiliaries or rheology auxiliaries.

The present application also comprises the use as phlegmatizers of 1,2-cyclohexanedicarboxylic acid esters selected from the group consisting of 1,2-diisobutylcyclohexanedicarboxylic acid ester, 1,2-di-(2-ethyl hexyl)-cyclohexane dicarboxylic acid ester and 1,2-diisononylcyclohexanedicarboxylic acid ester disclosed above. The 1,2-cyclohexanedicarboxylic acid esters are particularly preferably used as phlegmatizers for organic peroxides or nitrocellulose. Here, they can stabilize reactive/explosive products in order to provide safe transport and use of the products. Because the 1,2-cyclohexanedicarboxylic acid esters have chemical affinity for the reactive/explosive products, they have excellent suitability as phlegmatizers. The amounts used of the 1,2-cyclohexanedicarboxylic acid esters are those conventional for conventional phlegmatizers and are known to the person skilled in the art.

1,2-diisobutylcyclohexanedicarboxylic acid ester is preferably used in the calendering auxiliaries or rheology auxiliaries, or as calendaring auxiliaries or rheology auxiliaries.

By way of example, EP-A 0 772 609 discloses suitable compositions in which the 1,2-diisobutylcyclohexanedicarboxylic acid esters disclosed above, in particular the esters, can be used as phlegmatizers.

The 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester disclosed are moreover suitable for use in pharmaceutical products.

The present invention therefore also provides pharmaceutical products comprising at least one 1,2-cyclohexanedicarboxylic acid ester selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester.

In the pharmaceutical compositions, by way of example, the 1,2-cyclohexanedicarboxylic acid esters used according to the invention can be used as plasticizers in plastics, which are present in the pharmaceutical compositions, inter alia because they are toxicologically non-hazardous. The person skilled in the art is aware of suitable plastics, and also of suitable amounts of the at least one 1,2-cyclohexanedicarboxylic acid ester used as plasticizer.

1,2-diisobutylcyclohexanedicarboxylic acid ester is preferably used in the calendaring auxiliaries or rheology auxiliaries, or as calendering auxiliaries or rheology auxiliaries.

The 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester used according to the invention may moreover be used in what are known as time-release compositions, i.e. compositions with prolonged release of active ingredients in the form of medicaments and/or of nutrients, for example for oral administration. By way of example, EP-A 0 709 087 discloses suitable compositions.

1,2-diisobutylcyclohexanedicarboxylic acid ester is preferably used in the calendering auxiliaries or rheology auxiliaries, or as calendaring auxiliaries or rheology auxiliaries.

The 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester according to the present application can moreover be used as plasticizer in adhesives.

The present application therefore also provides an adhesive comprising at least one 1,2-cyclohexanedicarboxylic acid ester selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester.

These adhesives are capable of versatile use. By way of example, the adhesives comprising the 1,2-cyclohexanedicarboxylic acid esters disclosed may be used in the sector of paper and packaging, wood, in the construction sector, in the household, hobby, and office sectors, in the automotive industry, in the medical sector, in electronics, in shoe production, or else in adhesive tapes in the application sectors mentioned. In one preferred embodiment, the adhesives comprising the 1,2-cyclohexanedicarboxylic acid esters are used in the medical sector. This is advantageous because the 1,2-cyclohexanedicarboxylic acid esters used according to the invention do not give rise to allergies.

The 1,2-cyclohexanedicarboxylic acid esters used according to the invention may be used in the sectors mentioned in various types of adhesive for various applications. The sectors mentioned, and also the adhesives that are suitable, are described in more detail below:

Paper and Packaging

The adhesives comprising the 1,2-cyclohexanedicarboxylic acid esters used according to the invention are used for the production of impermeable packaging materials, such as composite films, or for the hermetic closure of packaging (e.g. coffee packs) for modern marketing, self-service, ready meals, and frozen food.

Adhesives resistant to low and high temperatures permit the production of freezer packaging and microwave packaging. The adhesives here for the production of packaging intended for food or drink have to comply with the strict regulations of food and drink legislation.

Other application sectors for the adhesives comprising the 1,2-cyclohexanedicarboxylic acid esters used according to the invention are the production of cigarettes and of labels, and also the production of paper and the production of newspapers, and the binding of books, catalogues, etc., and also adhesives for stamps and closures of mail envelopes.

Wood

Adhesives particularly suitable for application in the timber sector and comprising the 1,2-cyclohexanedicarboxylic acid esters used according to the invention are polycondensation adhesives, dispersion adhesives, and hot-melt adhesives. The composition of these adhesives is known to the person skilled in the art.

Construction Sector

The adhesives comprising the 1,2-cyclohexanedicarboxylic acid esters used according to the invention may be used in wallpapers, floorcoverings, e.g. composed of linoleum, rubber, or textile, and also tiles or parquet, or in double glazing.

Household Sector, Hobby Sector, and Office Sector

The adhesives comprising the 1,2-cyclohexanedicarboxylic acid esters used according to the invention may be used in universal adhesives, adhesive sticks, paper adhesives and DIY adhesives, contact adhesives, quick-setting adhesives, and also adhesives for plastic and cardboard, paperboard, photographs, and labels. They provide simple, clean, and rapid bonding, which is environmentally compatible because no solvent is used. The adhesives can also be used as model-building adhesives, assembly adhesives and 2-component adhesives. Preference is given here to water-based or solvent-free adhesive systems.

Automotive Industry

The adhesives comprising the 1,2-cyclohexanedicarboxylic acid esters used according to the invention are suitable for application in the automotive industry. By way of example, they are used in adhesives based on polyurethane or in 2-component adhesives. The composition of these adhesives is known to the person skilled in the art.

Medical Sector

The adhesives comprising the 1,2-cyclohexanedicarboxylic acid esters used according to the invention may be used, by way of example, in plasters, for the adhesive bonding of joint prostheses, in dental medicine for the adhesive bonding of bridges, crowns, veneers, and inlays, and for the production of any type of hygiene item, e.g. diapers, inserts, surgical drapes, and paper handkerchiefs. They are also used in the final production stages for medicaments in blister packs, in order to protect the tablets from moisture, dirt, and bacteria.

Electronics

Examples of use of the 1,2-cyclohexanedicarboxylic acid esters used according to the invention are found in photo initiated adhesive, sealing, and potting compositions for chip potting, in chip-on-board technology, for chip encapsulation, and also as flip-chip underfiller.

Shoe Production

Adhesive bonds in the shoe interior region use natural rubber adhesives, synthetic rubber adhesives, dispersion adhesives based on plastics polymers, or else water-based adhesives composed of starch, of dextrin, and of cellulose derivatives. All of these adhesives are mainly processed by the wet adhesion process. According to the invention, the adhesives mentioned comprise 1,2-cyclohexanedicarboxylic acid esters Suitable compositions of the adhesives are known to the person skilled in the art.

Hot-melt adhesives based on ethylene-vinyl acetate copolymers are used for lamination, and polyamide adhesives are used for edge-folding. According to the invention, these adhesives likewise comprise 1,2-cyclohexanedicarboxylic acid esters. Suitable compositions of the adhesives are known to the person skilled in the art.

The bonding of shoe upper to insole, termed "lasting", can use polyimide hot-melt adhesives or polyester hot-melt adhesives which likewise comprise the 1,2-cyclohexanedicarboxylic acid esters used according to the invention.

Adhesive bonding of the outsoles to the shoe upper can use solvent- or dispersion-type adhesives based on polychloroprene or on polyurethane, likewise comprising the cyclohexanepolycarboxylic acid derivatives used according to the invention.

Adhesive Tapes

The adhesives comprising the 1,2-cyclohexanedicarboxylic acid esters used according to the invention may moreover be used in adhesive tapes.

Self-adhesive tapes are produced as a way of solving problems in industry, for other commercial purchases, and also for the household market. A wide variety of very modern adhesive technologies is commercially available, providing individual problem solutions for all of the important applications, with emphasis on the packaging industry, electrical industry, transport industry, and paper industry.

Various demands are placed upon the significant properties of the products, e.g. bond strength, heat resistance, load-bearing capability, and tensile strength, these depending on the manner of use of the adhesive tapes. By way of example, adhesive tapes for masking during industrial painting procedures have to withstand high temperatures and have to be capable of subsequent, removal leaving no residue. However, the important factors in sheathing and bundling applications are high strength and low extendibility. In contrast, roll changes in the paper industry need immediate high bond strength. Outside the industrial application sectors, these products are mainly used in schools, in households, in offices, or in the DIY sector.

One or more of the following constituents may be present—beside the 1,2-cyclohexanedicarboxylic acid esters—in the inventive adhesives, and a fundamental distinction is drawn here between adhesives based on natural raw materials and those based on synthetic raw materials, but combinations of these starting materials are also possible. Suitable raw materials are known to the person skilled in the art.

By way of example, EP-A 0 928 207 discloses suitable compositions for the adhesives, in particular for use in the medical sector, e.g. as adhesive compositions for application to the skin of humans or of animals.

1,2-diisobutylcyclohexanedicarboxylic acid ester is preferably used in the calendering auxiliaries or rheology auxiliaries, or as calandaring auxiliaries or rheology auxiliaries.

The 1,2-cyclohexanedicarboxylic acid esters selected from the group consisting of 1,2-diisobutylcyclohexanedicarboxylic acid ester, 1,2-di-(2-ethylhexyl)cyclohexanedicarboxylic acid ester and 1,2-diisononylcyclohexanedicarboxylic acid ester used according to the invention are moreover suitable as plasticizers for impact modifiers, preferably for impact modifiers for thermoplastics, e.g. for polyamide. Suitable amounts used of the at least one 1,2-cyclohexanedicarboxylic acid ester used according to the invention are the conventional amounts for plasticizers and are therefore known to the person skilled in the art.

1,2-di-(2-ethylhexyl)-cyclohexanedicarboxylic acid ester and 1,2-diisononylcyclohexanedicarboxylic acid ester are preferably used in the emulsifiers, or as emulsifiers.

The 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester used according to the invention may moreover be used as auxiliaries during the production of detergents, e.g. as modifiers for retaining the free-flowability of detergent powders and converting them to a condition suitable for use. Suitable amounts are the amounts of modifiers usually used in detergents, and are known to the person skilled in the art.

1,2-di-(2-ethylhexyl)-cyclohexanedicarboxylic acid ester and 1,2-diisononylcyclohexanedicarboxylic acid ester are preferably used in the emulsifiers, or as emulsifiers Each of the inventive auxiliaries which comprise the 1,2-cyclohexanedicarboxylic acid esters used according to the invention is prepared by the process known to the person skilled in the art.

The invention claimed is:

1. Surface-active compositions selected from defoamers, antifoams, and emulsifiers comprising 1,2-cyclohexanedicarboxylic acid esters selected from the group consisting of 1,2-diisobutylcyclohexanedicarboxylic acid ester, 1,2-di-(2-ethylhexyl)-cyclohexanedicarboxylic acid ester and 1,2-diisononylcyclohexanedicarboxylic acid ester, wherein at least one 1,2-cyclohexanedicarboxylic acid ester is 1,2-diisononylcyclohexanedicarboxylic acid ester wherein the proportion of the at least one 1,2-cyclohexanedicarboxylic acid ester is 0.1 to 5% by weight and wherein a nonanol mixture used for preparation of the 1,2-diisononylcyclohexanedicarboxylic acid ester has the following composition:

A. from 1.73 to 3.73% by weight of 3-ethyl-6-methylhexanol;
   from 0.38 to 1.38% by weight of 2,6-dimethylheptanol;
   from 2.78 to 4.78% by weight of 3,5-dimethylheptanol;
   from 6.30 to 16.30% by weight of 3,6-dimethylheptanol;
   from 5.74 to 11.74% by weight of 4,6-dimethylheptanol;
   from 1.64 to 3.64% by weight of 3,4,5-trimethylhexanol;
   from 1.47 to 5.47% by weight of 3,4,5-trimethylhexanol, 3-methyl-4-ethylhexanol, and 3-ethyl-4-methylhexanol;
   from 4.00 to 10.00% by weight of 3,4-dimethylheptanol;
   from 0.99 to 2.99% by weight of 4-ethyl-5-methylhexanol, and 3-ethylheptanol;
   from 2.45 to 8.45% by weight of 4-dimethylheptanol and 3-methyloctanol;
   from 1.21 to 5.21% by weight of 4,5-dimethylheptanol;
   from 1.55 to 5.55% by weight of 5,6-dimethylheptanol;
   from 1.63 to 3.63% by weight of 4-methyloctanol;
   from 0.98 to 2.98% by weight of 5-methyloctanol;
   from 0.70 to 2.70% by weight of 3,6,6-trimethylhexanol;
   from 1.96 to 3.96% by weight of 7-methyloctanol;
   from 1.24 to 3.24% by weight of 6-methyloctanol;
   from 0.1 to 3% by weight of n-nonanol;
   from 25 to 35% by weight of other alcohols having 9 or 10 carbon atoms, and
   wherein the entirety of the components mentioned giving 100% by weight or B. from 6.0 to 16.0% by weight of n-nonanol;
   12.8 to 28.8% by weight of 6-methyloctanol;
   12.5 to 28.8% by weight of 4-methyloctanol;
   3.3 to 7.3% by weight of 2-methyloctanol;
   5.7 to 11.7% by weight of 3-ethylheptanol;
   1.9 to 3.9% by weight of 2-ethylheptanol;
   1.7 to 3.7% by weight of 2-propylhexanol;
   3.2 to 9.2% by weight of 3,5-dimethylheptanol;
   6.0 to 16.0% by weight of 2,5-dimethylheptanol;
   1.8 to 3.8% by weight of 2,3-dimethylheptanol;
   0.6 to 2.6% by weight of 3-ethyl-4-methylhexanol;
   2.0 to 4.0% by weight of 2-ethyl-4-methylhexanol;
   0.5 to 6.5% by weight of other alcohols having 9 carbon atoms; and
   wherein the entirety of the components mentioned gives 100% by weight.

2. Surface active compositions according to claim 1, wherein the cyclohexanepolycarboxylic acid derivative is obtainable via hydrogenation of a benzenepolycarboxylic acid or of a derivative thereof, or via hydrogenation of a mixture composed of two or more thereof, by bringing the benzenepolycarboxylic acid or the derivative thereof or the mixture composed of two or more thereof into contact with a hydrogen-containing gas in the presence of a catalyst which comprises, as active metal, at least one metal of the 8th transition group of the Periodic Table of the Elements alone or together with at least one metal of the 1st or 7th transition group of the Periodic Table of the Elements, applied to a support which has macropores.

3. The surface-active compositions as claimed in claim 1, wherein the surface-active compositions are defoamers.

4. The surface-active compositions as claimed in claim 1, wherein the surface-active compositions are antifoams.

5. The surface-active compositions as claimed in claim 1, wherein the surface-active compositions are emulsifiers.

* * * * *